United States Patent [19]
Keith

[11] Patent Number: 5,312,340
[45] Date of Patent: May 17, 1994

[54] BALLOON DILATATION CATHETER HAVING DUAL SEALING PLUGS

[75] Inventor: Peter T. Keith, Fridley, Minn.

[73] Assignee: SciMed Life Systems, Inc., Maple Grove, Minn.

[21] Appl. No.: 852,546

[22] Filed: Mar. 17, 1992

[51] Int. Cl.⁵ ............................................. A61M 29/00
[52] U.S. Cl. ...................................... 604/96; 606/194
[58] Field of Search ................... 604/96, 167, 95, 101; 606/194, 192, 195

[56] References Cited

U.S. PATENT DOCUMENTS

| | | |
|---|---|---|
| 3,402,717 | 9/1968 | Doherty . |
| 3,837,347 | 9/1974 | Tower . |
| 4,261,339 | 4/1981 | Hanson et al. . |
| 4,413,989 | 11/1983 | Schjeldahl et al. . |
| 4,606,347 | 8/1986 | Fogarty et al. . |
| 4,616,653 | 10/1986 | Samson et al. . |
| 4,715,378 | 12/1987 | Pope, Jr. et al. . |
| 4,771,778 | 9/1988 | Mar . |
| 4,793,350 | 12/1988 | Mar et al. . |
| 4,813,934 | 3/1989 | Engelson et al. . |
| 4,821,722 | 4/1989 | Miller et al. . |
| 4,838,268 | 6/1989 | Keith et al. . |
| 4,846,174 | 7/1989 | Willard et al. . |
| 4,848,344 | 7/1989 | Sos et al. . |
| 4,917,088 | 4/1990 | Crittenden . |
| 4,943,278 | 7/1990 | Euteneuer et al. . |
| 4,964,409 | 10/1990 | Tremulis . |
| 4,976,720 | 12/1990 | Machold et al. . |
| 4,998,917 | 3/1991 | Gaiser et al. . |
| 4,998,923 | 3/1991 | Samson et al. ................... 604/96 |
| 5,002,559 | 3/1991 | Tower . |
| 5,003,989 | 4/1991 | Taylor et al. . |
| 5,032,113 | 7/1991 | Burns .............................. 604/96 |
| 5,042,985 | 8/1991 | Elliott et al. ................. 604/96 X |
| 5,055,109 | 10/1991 | Gould et al. . |
| 5,059,176 | 10/1991 | Winters . |
| 5,102,390 | 4/1992 | Crittenden et al. . |
| 5,104,376 | 4/1992 | Crittenden . |
| 5,135,487 | 8/1992 | Morrill et al. . |
| 5,135,494 | 8/1992 | Engelson et al. . |
| 5,141,518 | 8/1992 | Hess et al. . |
| 5,156,595 | 10/1992 | Adams . |
| 5,171,221 | 12/1992 | Samson ....................... 604/167 X |
| 5,195,989 | 3/1993 | Euteneuer . |
| 5,209,728 | 5/1993 | Kraus et al. . |
| 5,246,420 | 9/1993 | Kraus et al. . |

FOREIGN PATENT DOCUMENTS

| | | |
|---|---|---|
| 0368523A2 | 10/1989 | European Pat. Off. . |
| 0462801A1 | 6/1991 | European Pat. Off. . |
| 0528294A2 | 8/1992 | European Pat. Off. . |
| WO91/13649 | 9/1991 | World Int. Prop. O. . |

Primary Examiner—John D. Yasko
Attorney, Agent, or Firm—Nawrocki, Rooney & Sivertson

[57] ABSTRACT

A non-over-the-wire catheter for use in angioplasty including a core wire which extends distally beyond a distal end of a tubular member. The tubular member defines an interior passage which is in fluid communication with a distal interior passage of a waist tube that extends about the core wire. An inflatable balloon member extends about the core wire and is in fluid communication with the distal interior passage of the waist tube. A distal end of the balloon member extends coaxially about a portion of the core wire so as to allow rotational movement of the core wire relative to the balloon member. First and second sealing plugs are secured to the core wire proximal to and distal of, respectively, the distal end of the balloon member. The sealing plugs provide resistance to flow of pressurized balloon fluid to minimize leakage through the distal end of the balloon member. The first and second sealing plugs also prevent the waist tube and balloon member from being displaced axially relative to the core wire.

16 Claims, 3 Drawing Sheets

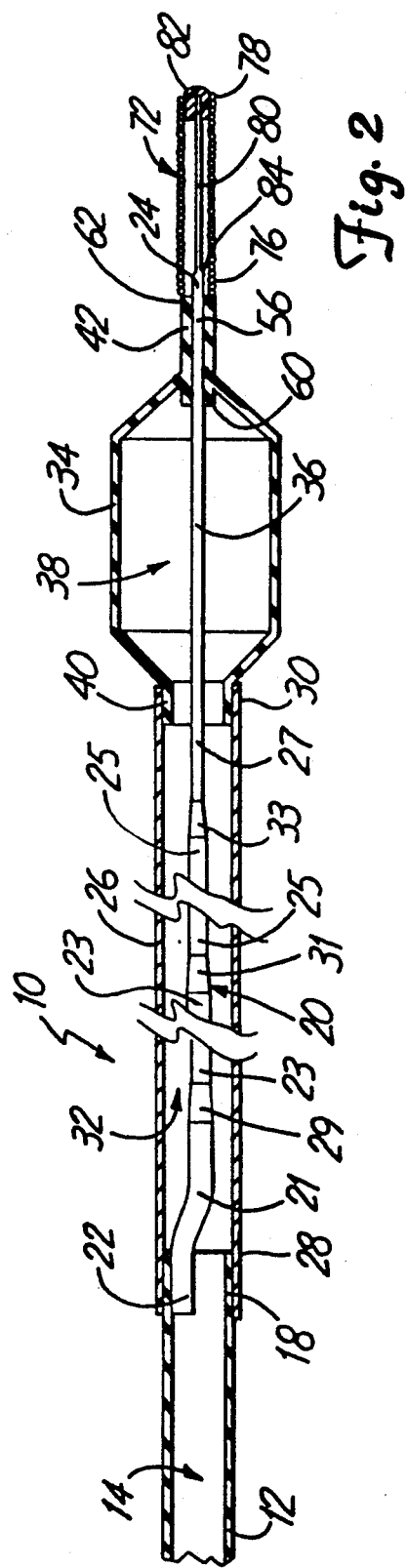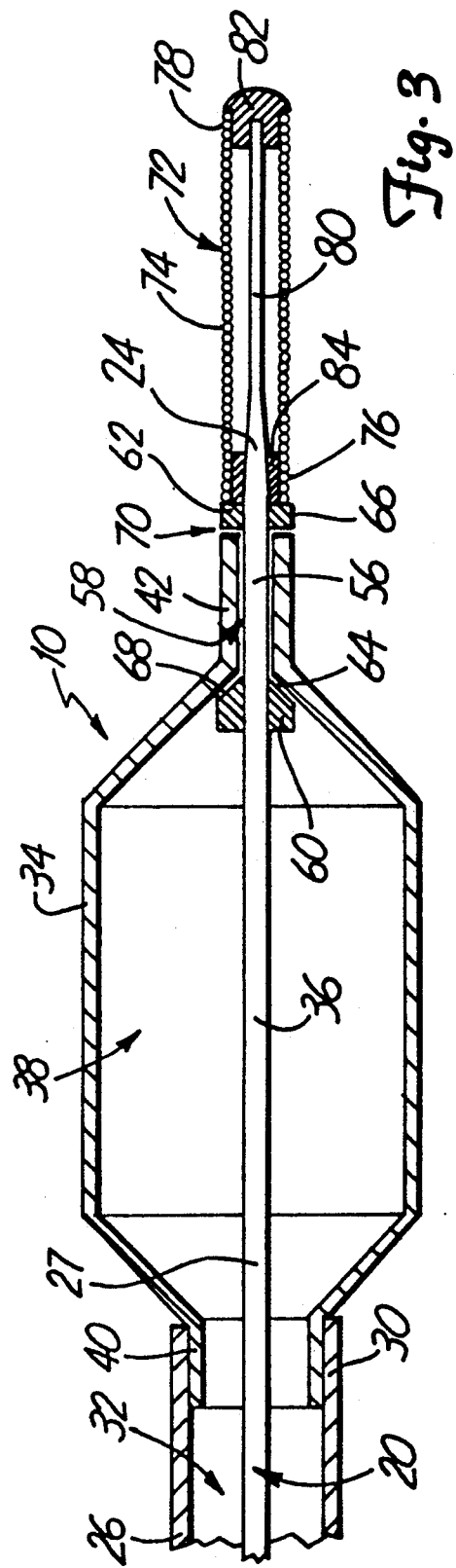

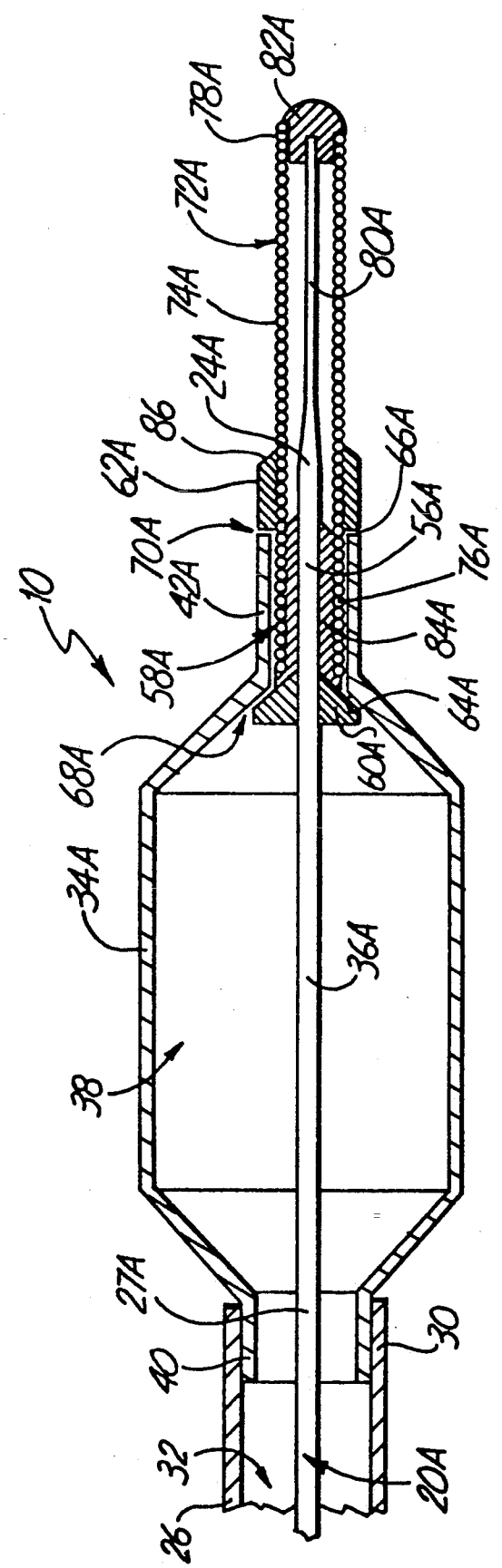

BALLOON DILATATION CATHETER HAVING DUAL SEALING PLUGS

REFERENCE TO COPENDING APPLICATIONS

Reference is made to the following commonly assigned applications which were filed on even date with this application and are entitled as follows:

(1) Balloon Dilatation Catheter Having A Free Core Wire (Ser. No. 07/852,545); and (2) Balloon Dilatation Catheter Having A Torsionally Soft Component (Ser. No. 07/852,597).

BACKGROUND OF THE INVENTION

The present invention relates to the field of percutaneous transluminal coronary angioplasty (PTCA). In particular, the present invention is a non-over-the-wire dilatation balloon catheter.

Angioplasty has gained wide acceptance in recent years as an efficient and effective method for treating certain types of vascular diseases. In particular, angioplasty is widely used for opening stenoses in the coronary arteries, although it is also used for treatment of stenoses in other parts of the vascular system.

The most widely used form of angioplasty makes use of a dilatation catheter which has an inflatable balloon at its distal end. Typically, the catheter is introduced and directed partially through a patient's vascular system via a guide catheter. Using fluoroscopy, a physician guides the catheter through that portion of the patient's vascular system distal of the guide catheter until the balloon is positioned across the stenosis. While the catheter is being steered through the vascular system, the balloon is in a deflated state, wrapped (i.e., folded) tightly about the distal end of the catheter to reduce the profile of the balloon. Reducing the profile of the balloon allows the catheter to easily travel through the guide lumen of the guide catheter and traverse arterial vessels and stenoses having small through openings. Once the catheter is positioned with the balloon across the stenosis, the balloon is inflated by supplying fluid under pressure through an inflation lumen to the balloon. Inflation of the balloon causes stretching of the artery and pressing of the lesion into the artery wall to re-establish an acceptable blood flow through the artery.

Over-the-wire catheters and non-over-the-wire catheters are two types of dilatation catheters that are commonly used in angioplasty. An over-the-wire catheter has an inflation lumen and a guide wire lumen through which a separate guide wire is advanced to establish a path to the stenosis. Since the guide wire is separate from the catheter, torque applied to the guide wire to steer the guide wire through the vascular system and across the stenosis is not conveyed to any part of the catheter. Once a distal end of the guide wire is across the stenosis, the separate over-the-wire catheter is advanced over the guide wire until the balloon is positioned across the lesion.

One type of non-over-the-wire catheter has its own built in guide wire (sometimes referred to as a core wire) such that the core wire, balloon and inflation lumen comprise a single unit. Due to this single unit construction, torque (i.e., a rotational force) applied to a proximal end of a hypotube of the non-over-the-wire catheter (to which the core wire is fixedly attached) to steer the catheter through the vascular system and across the stenosis, is conveyed to other parts of the catheter.

In particular, torque induced rotation applied to the hypotube and core wire combination is transmitted to a distal end of the balloon and to a proximal end of a waist tube that extends about the core wire and couples the hypotube to the balloon. However, due to the tortuosity of portions of the guide catheter and of the patient's vascular system, the balloon and the waist tube may contact parts of the walls of the guide catheter guide lumen and the arterial vessels. This contact may cause rotation of portions of the balloon and the waist tube to lag behind rotation of the hypotube and core wire combination. The lag in balloon rotation dampens steering responsiveness of the balloon catheter itself, since contact of the balloon with the walls of the guide lumen and arterial vessels imparts drag to the distal end of the core wire. This, in turn, dampens the responsiveness of the core wire distal spring tip.

Typically, a spring tip is provided at the distal end of the core wire and is formed with a J-bend. The J-bend permits the balloon catheter to be steered into desired arterial branches. That is, torque induced rotation applied to the hypotube is transmitted to the spring tip through the core wire to position the J-bend to enter the desired arterial branch. A non-uniform ability to accurately position the J-bend of the spring tip, such as may be caused by a lag in balloon rotation which dampens steering responsiveness, makes the balloon catheter difficult to steer and may unnecessarily prolong the angioplasty procedure.

In addition, the lag in balloon rotation causes the balloon and the waist tube to twist upon themselves. The balloon tends to twist upon itself proximally from its distal attachment to the core wire, while the waist tube twists upon itself distally from its proximal attachment to the hypotube. If balloon twist is minimal, as a result of minimal steering torque applied to the hypotube, the balloon will untwist upon application of inflation fluid pressure to inflate the balloon once the balloon is positioned across a stenosis. However, if balloon twist is significant, the balloon may not inflate uniformly. Non-uniform balloon inflation exhibits balloon behavior wherein portions of the balloon (i.e., constrictions in the balloon due to twist) do not inflate to their maximum diameter. These under-inflated constrictions do not uniformly press the stenosis into the arterial wall and hence, do not effectively dilate the lesion to allow acceptable blood flow through the arterial vessel. In addition, upon deflation of the balloon, those segments of the balloon (i.e., segments adjacent the constrictions) which were fully inflated may not completely deflate. These partially deflated segments may make withdrawal of the balloon catheter from the patient's vascular system back through the guide catheter difficult.

It is desirable in a non-over-the-wire catheter to reduce the transmission of torque (applied to the hypotube and core wire combination) to the balloon of the catheter. The reduction in torque transmission would abate twisting of the balloon as the catheter is steered through the vascular system, and thereby permit uniform inflation and deflation of the balloon which is needed to effectively dilate the stenosis to re-establish an acceptable blood flow through the arterial vessel. In addition, the reduction in torque transmission, from the core wire to the balloon, would reduce, if not eliminate, the twisting of the balloon from the lag in balloon rotation upon the application of torque to the core wire.

This reduction in balloon twist would alleviate steering difficulties sometimes associated with non-over-the-wire catheters wherein torque is readily transmitted from the core wire to the balloon.

SUMMARY OF THE INVENTION

The present invention is a catheter for use in angioplasty. The catheter includes an elongate flexible tubular member having an interior passage extending from a proximal end to a distal end. A guiding member having proximal and distal ends is secured at its proximal end to the tubular member adjacent its distal end, so that the guiding member extends distally beyond the distal end of the tubular member. An elongate flexible waist tube having proximal and distal ends is sealably connected at its proximal end to the tubular member adjacent its distal end, such that the waist tube extends distally beyond the distal end of the tubular member about the guiding member to define a distal interior passage in fluid communication with the interior passage of the tubular member. An inflatable balloon member extends around a section of the guiding member and has an interior in fluid communication with the distal interior passage of the waist tube. The balloon member includes a proximal end sealably connected to the distal end of the waist tube, and a distal end that extends coaxially about a portion of the guiding member so as to allow rotational movement of the guiding member relative to the balloon member, while restricting fluid flow through the distal end of the balloon member. A sealing means associated with the guiding member and cooperable with the distal end of the balloon member also restricts the flow of fluid through the distal end of the balloon member.

In one embodiment, an inside diameter of the distal end of the balloon member is greater than the diameter of the portion of the guiding member within it to define a minimal cylindrical gap. The cylindrical gap allows rotational movement of the guiding member relative to the balloon member, while providing resistance to flow of pressurized balloon fluid. This resistance minimizes leakage of balloon fluid through the distal end of the catheter during inflation and deflation of the balloon member.

The sealing means is defined by first and second sealing plugs that are secured to the guiding member proximal of and distal to, respectively, the distal end of the balloon member. The first and second sealing plugs are spaced from the inner and outer edges, respectively, of the distal end of the balloon member to define gaps that permit rotational movement of the guiding member relative to the balloon member while also providing resistance to flow of pressurized balloon fluid to help minimize leakage of balloon fluid through the distal end of the balloon member. The first and second sealing plugs also prevent the waist tube and balloon member from being displaced axially relative to the core wire.

In a first embodiment, the catheter includes a radiopaque spring tip positioned distally of the distal end of the balloon member. In an alternative embodiment, a proximal end of the spring tip extends about the portion of the guiding member into the distal end of the balloon member. In this latter embodiment, the inside diameter of the distal end of the balloon member is greater than an outside diameter of the coil member to define a minimal cylindrical gap. As in the first embodiment, the cylindrical gap permits rotational movement of the guiding member relative to the balloon member, while providing resistance to flow of pressurized balloon fluid to minimize leakage of balloon fluid through the distal end of the balloon member. In the alternative embodiment, the second sealing plug is secured about the coil member immediately distal of the outer edge of the distal end of the balloon member.

The non-over-the-wire catheter of the present invention is relatively uncomplicated and since the distal end of the balloon member is not attached to the distal end of the guiding member, the guiding member can be rotated relative to the balloon member which reduces twisting of the balloon member as the catheter is steered through the vascular system of a patient. The reduction in balloon twist permits uniform inflation and deflation of the balloon which is needed to effectively dilate the stenosis and re-establish acceptable blood flow through the arterial vessel.

Moreover, the non-transmission of torque from the guiding member to the balloon member reduces, if not eliminates balloon rotation. Hence, the effects (i.e., dampened steering responsiveness) due to the lag in balloon rotation upon application of torque to the guiding member are substantially decreased. The effects of balloon rotation lag are decreased and steering responsiveness improved, because contact between the balloon and the interior wall of a guide catheter and the walls of arterial vessels no longer imparts drag to the distal end of the guiding member. This lack of drag alleviates steering difficulties sometimes associated with non-over-the-wire catheters wherein torque is readily transmitted from the guiding member to the balloon.

In addition, the first and second sealing plugs substantially restrict the flow of pressurized balloon fluid distally through the distal end of the balloon member, and the flow of intravascular fluid proximally through the distal end of the balloon member and into the interior passages of the catheter to minimize any catheter leakage. Moreover, the first and second sealing plugs define first and second stops, respectively, that prevent the balloon member and waist tube from being displaced proximally or distally, respectively, along the guiding member as the catheter is being maneuvered through a vascular system of a patient.

BRIEF DESCRIPTION OF THE DRAWINGS

FIG. 2 is an enlarged sectional view of a first preferred embodiment of a distal end of the balloon catheter shown in FIG. 1.

FIG. 3 is a greatly enlarged sectional view similar to FIG. 2 showing details of the distal end of the first preferred embodiment of the balloon catheter.

FIG. 4 is a greatly enlarged sectional view showing details of an alternative embodiment of a distal end of the balloon catheter in accordance with the present invention.

DETAILED DESCRIPTION OF THE PREFERRED EMBODIMENTS

Figure 1:
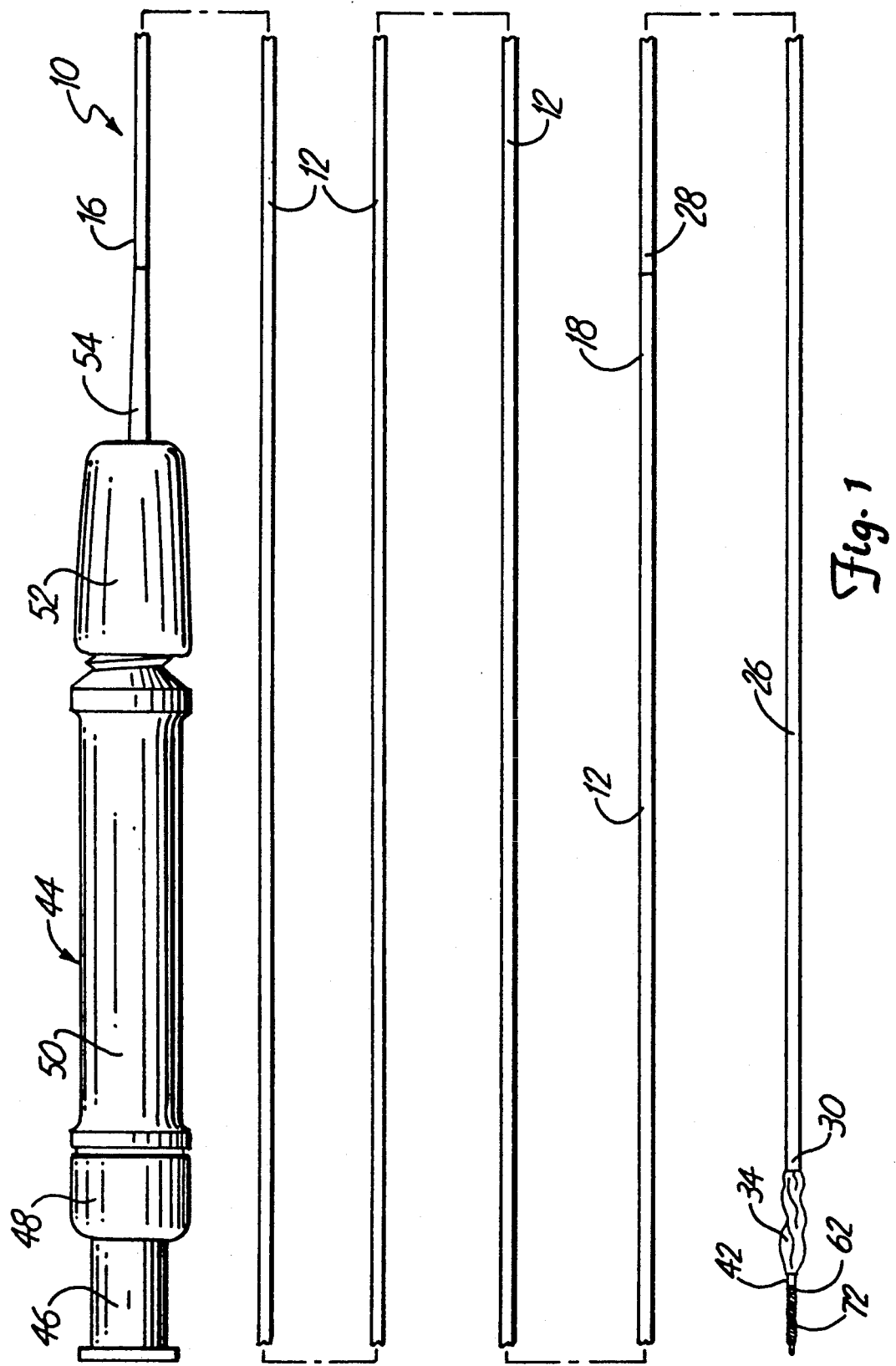
FIG. 1 is an elevational view of a balloon catheter in accordance with the present invention.

A non-over-the-wire catheter 10 in accordance with the present invention is illustrated generally in FIG. 1. The catheter 10 includes an elongate flexible tubular member (i.e., hypotube) 12 having an interior passage 14 (See FIG. 2) extending from a proximal end 16 to a distal end 18. As seen best in FIG. 2, a core wire 20 has a proximal end 22 and a distal end 24. The proximal end 22 of the core wire 20 is joined to the tubular member 12 adjacent to its distal end 18, with the core wire 20 extending distally beyond the distal end 18 of the tubular member 12.

The core wire 20 preferably provides varying flexibility along its length such that its flexibility increases in the distal direction. As illustrated in FIG. 2 (not shown to scale), this may be accomplished by having a core wire with one or more ground tapers. In one embodiment, the tubular member 12 is preferably formed from Type 304 stainless steel hypodermic tubing, and the core wire 20 is preferably formed from Type 304 stainless steel and manufactured by centerless grinding. The core wire 20 preferably has four main sections 21, 23, 25 and 27 and three tapered sections 29, 31 and 33. The core wire 20 is preferably stress relieved by exposing the wires before grinding to a temperature in a range of from 500° F. to 800° F. for a time period from about 30 min. to about 6 hours, and preferably at 750° F. for about 5 hours including ramp-up time. Preferably, the first section 21 is approximately 1.25 in. long and has a diameter of approximately 0.012 in. The second section 23 is approximately 4 in. long and has a diameter of approximately 0.0095 in. The third section 25 is approximately 3 in. long and has a diameter of approximately 0.0075 in. The fourth section 27 is approximately 2.5 in. long and has a diameter of approximately 0.0053 in. The first, second and third tapered sections 29, 31 and 33, respectively, are each approximately 1 in. in length.

The core wire 20 is preferably joined to the tubular member 12 by a braze material composed of a silver brazing metal powder with a brazing flux such as (BAg-7-325 mesh) available from Turbo-Braze Corp. (Union, New Jersey). Alternatively, the core wire 20 can be joined to the tubular member 12 by a silver solder material composed of 4% silver and 96% tin.

Other materials, such as a super elastic alloy (otherwise known as a shape memory alloy) may be used for the tubular member 12. For example, TINEL available from Raychem Corp. (Menlo Park, California) or a Nickel-Titanium shape memory alloy available from Shape Memory Applications, Inc. (Sunnyvale California). An adhesive material, such as cyanoacrylate, may be used to join a core wire 20 to a tubular member 12 composed of a super elastic alloy.

The catheter 10 further includes an elongate flexible waist tube 26 having a proximal end 28 and a distal end 30. The proximal end 28 of the waist tube 26 is sealably connected to the tubular member 12 adjacent its distal end 18. As seen best in FIG. 2, the waist tube 26 extends distally beyond the distal end 18 of the tubular member 12 and about the core wire 20 to define a distal interior passage 32. The distal interior passage 32 is in fluid communication with the interior passage 14 of the tubular member 12.

As seen in FIG. 2, an inflatable balloon member 34 extends about a section 36 of the core wire 20. The balloon member 34 has an interior 38 in fluid communication with the distal interior passage 32 of the waist tube 26. The balloon member 34 further includes a proximal end 40 and a distal end 42. The proximal end 40 of the balloon member 34 is sealably connected to the distal end 30 of the waist tube 26.

In one embodiment, the waist tube 26 is preferably formed of a polymer material, such as polyethelene. For example, PETROTHENE (HD, LB5003, HDPE) available from Quantum, USI Division (Cincinnati, Ohio). The balloon member 34 is preferably formed of a polymer material such as polyolefin which has been treated by radiation cross linking. The balloon member 34 may also be silicone coated. A suitable polyolefin is available from E. I. DuPont Nemours & Co. (Wilmington, Delaware) under the tradename SURYLYN® (8527 POC) Ionomer. The waist tube 26 is preferably bonded to the tubular member 12 and to the balloon member 34 by a suitable adhesive and sealing material. For example, LOCTITE PRISM 405, a cyanoacrylate, available from Loctite, Corp. (Newington, Connecticut) or TRA-BOND 2135D, an epoxy, available from Tra-Con, Inc. (Medford, Massachusetts).

As seen in FIG. 1, a manifold fitting 44 is mounted on the proximal end 16 of the tubular member 12 to facilitate connection with an inflation device (not shown) for the introduction and removal of pressurized balloon fluid to the catheter 10 to inflate and deflate the balloon member 34 via interior passage 14 and distal interior passage 32. The manifold fitting 44 includes a luer fitting 46 (for connection to the inflation device), a first end cap 48, a manifold body 50, a second end cap 52 and a strain relief tube 54.

In the preferred embodiment shown in FIGS. 2 and 3, the distal end 42 of the balloon member 34 extends coaxially about a portion 56 of the core wire 20. An inside diameter of the distal end 42 of the balloon member 34 is greater than the diameter of the portion 56 of the core wire 20 to define a cylindrical gap 58 (on the order of 0.0001"–0.0003") between the portion 56 and the distal end 42. The cylindrical gap 58 is dimensioned to allow rotational movement of the core wire 20 relative to the balloon member 34, while providing resistance to flow of pressurized balloon fluid to minimize leakage of balloon fluid through the distal end 42 during inflation and deflation of the balloon member 34. Alternatively, the cylindrical gap 58 may be filled with a high viscosity fluid, such as silicone fluid, to aid in minimizing leakage of balloon fluid through the distal end 42 of the balloon member 34.

As seen best in FIG. 3, the catheter 10 further includes a sealing means defined by first and second sealing plugs 60 and 62, respectively. The first sealing plug 60 is secured to the core wire 20 immediately, proximally of an inner edge 64 of the distal end 42 of the balloon member 34. The second sealing plug 62 is secured to the core wire 20 immediately, distally of an outer edge 66 of the distal end 42 of the balloon member 34. The first sealing plug 60 has a tapered portion 67 that decreases distally and matches the taper at the inner edge 64 of the distal end 42.

The first and second sealing plugs 60 and 62 are spaced from the inner and outer edges 64 and 66, respectively, of the distal end 42 of the balloon member 34. The space between the first sealing plug 60 and the inner edge 64 of the distal end 42 defines a minimal conical gap 68 (on the order of 0.0001"–0.0003"), while the space between the second sealing plug 62 and the outer edge 66 of the distal end 42 defines a minimal radial gap 70 (on the order of 0.0001"–0.0003"). The conical gap 68 and the radial gap 70 permit rotational movement of the core wire 20 relative to the balloon member 34 while providing resistance to flow of pressurized balloon fluid to minimize leakage of balloon fluid through the distal end 42 during inflation and deflation of the balloon member 34.

As seen in FIG. 3, the catheter 10 includes a radiopaque spring tip 72 positioned distally of the distal end 42 and the second sealing plug 62. The spring tip 72 includes a flexible, helical coil member 74 having a proximal end 76 and a distal end 78. The helical coil member 74 is preferably formed from a radiopaque platinum alloy wire composed of 90% Pt and 10% Ir. The spring tip 72 is preferably 25 mm in length with varying flexibility. Alternatively, the spring tip 72 may be 15 mm in length with varying flexibility. A shaping ribbon 80 is integral with the core wire 20. A first joint 82, preferably comprising a weld, connects the distal end 78 of the coil member 74 to the shaping ribbon 80. A second joint 84 couples the proximal end 76 of the coil member 74 to the distal end 24 of the core wire 20. The second joint 84 preferably comprises a solder joint consisting of a silver solder material composed of 4% silver and 96% tin. Alternatively, the second joint 84 may comprise a braze joint consisting of a braze material composed of a silver brazing metal powder with a brazing flux such as (BAg-7-325 mesh) available from Turbo-Braze Corp. (Union, New Jersey). In the embodiment illustrated in FIGS. 2 and 3, the entire length of the coil member 74 extends distally beyond the distal end 42 of the balloon member 34.

In an alternative embodiment illustrated in FIG. 4, the proximal end 76A of the coil member 74A is secured by the second joint 84A about the core wire 20A at the portion 56A. In this embodiment, the inside diameter of the distal end 42A of the balloon member 34A is greater than an outside diameter of the coil member 74A to define the minimal cylindrical gap 58A between the coil member 74A and the distal end 42A. As in the previous embodiment, the cylindrical gap 58A permits rotational movement of the core wire 20A relative to the balloon member 34A, while providing resistance to flow of pressurized balloon fluid to minimize leakage of balloon fluid through the distal end 42A. In addition, in the alternative embodiment of FIG. 4, the second sealing plug 62A is secured about the coil member 74A immediately distal of the outer edge 66A of the distal end 42A of the balloon member 34A. A distal end 86 of the second sealing plug 62A is beveled to provide a smooth profile as the catheter 10 is maneuvered through a vascular system of a patient.

In one embodiment, the first and second sealing plugs 60, 60A and 62, 62A, respectively are preferably formed of a braze material composed of a silver brazing metal powder with a brazing flux, such as (BAg-7-325 mesh) available from Turbo-Braze Corp. (Union, New Jersey) and a radiopaque compound, such as platinum. The radiopaque compound facilitates fluoroscopy viewing of the catheter 10. Alternatively, the first and second sealing plugs 60, 60A and 62, 62A, respectively, could be formed of an adhesive material containing a radiopaque compound or a polymer material containing a radiopaque compound.

The non-over-the-wire catheter 10 of the present invention is relatively uncomplicated and since the distal end 42, 42A of the balloon member 34, 34A is not attached to the distal end 24, 24A of the core wire 20, 20A, the core wire 20, 20A can be rotated relative to the balloon member 34, 34A which reduces twisting of the balloon member 34, 34A as the catheter 10 is steered through the vascular system of a patient. The reduction in balloon twist permits uniform inflation and deflation of the balloon member 34, 34A which is needed to effectively dilate the stenosis and re-establish acceptable blood flow through the arterial vessel.

Moreover, the non-transmission of torque from the core wire 20, 20A to the balloon member 34, 34A reduces, if not eliminates balloon rotation. Hence, the effects (i.e., dampened steering responsiveness) due to the lag in balloon rotation upon application of torque to the core wire 20, 20A are substantially decreased. The effects of balloon rotation lag are decreased and steering responsiveness improved, because contact between the balloon member 34, 34A and the wall of a guide lumen of a guide catheter and the walls of arterial vessels no longer imparts drag to the distal end 24, 24A of the core wire 20, 20A. This lack of drag alleviates steering difficulties sometimes associated with non-over-the-wire catheters wherein torque is readily transmitted from the core wire to the balloon.

In addition, the first and second sealing plugs 60, 60A and 62, 62A, respectively, substantially restrict the flow of pressurized balloon fluid distally through the distal end 42, 42A, and the flow of intravascular fluid proximally through the distal end 42, 42A and into the interior passages 14 and 32 of the catheter 10 further minimizing catheter leakage. Moreover, the first and second sealing plugs 60, 60A and 62, 62A define first and second stops, respectively, that prevent the balloon member 34, 34A and waist tube 26 from being displaced proximally or distally, respectively, along the core wire 20, 20A as the catheter 10 is being maneuvered through a vascular system of a patient.

Although the present invention has been described with reference to preferred embodiments, workers skilled in the art will recognize that changes may be made in form and detail without departing from the spirit and scope of the invention. For example, in considering a preferred commercial embodiment of the catheter of the present invention, it is contemplated that the distal end of the catheter would include a strain relief assembly as disclosed in the commonly assigned application entitled Dilatation Catheter Strain Relief Assembly (Ser. No. 07/852,548) which was filed on even date with this application and which is hereby incorporated herein in its entirety by reference thereto.

What is claimed is:
1. A catheter comprising:
   a tube having a through passage extending from a proximal end to a distal end;
   a guiding member having a proximal end and a distal end, with the guiding member extending distally beyond the distal end of the tube;
   an inflatable balloon member extending around a section of the guiding member and having an interior in fluid communication with the through passage of the tube, the balloon member including a proximal end sealably connected to the distal end of the tube and a distal end extending coaxially about a portion of the guiding member so as to allow rotational movement of the guiding member relative to the balloon member; and
   a sealing means associated with the guiding member and cooperable with the distal end of the balloon member to substantially restrict the flow of fluid through the distal end of the balloon member, the sealing means including a first sealing plug secured tot he guiding member immediately, proximally of the distal end of the balloon member, and a second sealing plug secured to the guiding member immediately, distally of the distal end of the balloon member.
2. The catheter of claim 1 wherein the tube includes:
   an elongate flexible tubular member having an interior passage extending from a proximal end to a distal end; and a flexible waist tube having a proximal end and a distal end, the waist tube having its proximal end sealably connected to the tubular member, the waist tube extending distally beyond the distal end of the tubular member about the guiding member to define a distal interior passage in fluid communication with the interior passage of the tubular member.

3. The catheter of claim wherein an inside diameter of the distal end of the balloon member is greater than the diameter of the portion of the guiding member to define a minimal cylindrical gap between the portion of the guiding member and the distal end of the balloon member, the cylindrical gap allowing rotational movement of the guiding member relative to the balloon member while providing resistance to flow of pressurized balloon fluid to minimize leakage of balloon fluid through the distal end of the balloon member.

4. The catheter of claim 1, and further including:
a flexible, helical coil member having a proximal end and a distal end, the coil member being mounted on the distal end of the guiding member.

5. The catheter of claim 4 wherein the entire coil member extends distally beyond the distal end of the balloon member.

6. The catheter of claim 4, and further including:
a shaping ribbon extending between and connecting the distal end of the coil member to the distal end of the guiding member.

7. The catheter of claim 6 wherein a first fused joint connects the distal end of the coil member to the shaping ribbon, and wherein a second fused joint couples the proximal end of the coil member to the distal end of the guiding member.

8. The catheter of claim 4 wherein the proximal end of the coil member extends about the portion of the guiding member, and wherein an inside diameter of the distal end of the balloon member is greater than an outside diameter of the coil member to define a minimal cylindrical gap between the coil member and the distal end of the balloon member, the cylindrical gap allowing rotational movement of the guiding member relative to the balloon member while providing resistance to flow of pressurized balloon fluid to minimize leakage of balloon fluid through the distal end of the balloon member.

9. The catheter of claim 1 wherein the first sealing plug is spaced from an inner edge of the distal end of the balloon member to define a minimal conical gap between the first sealing plug and the inner edge of the distal end of the balloon member, the conical gap allowing rotational movement of the guiding relative to the balloon member while providing resistance to flow of pressurized balloon fluid to minimize leakage of balloon fluid through the distal end of the balloon member.

10. The catheter of claim 9 wherein the second sealing plug is spaced from an outer edge of the distal end of the balloon member to define a minimal radial gap between the second sealing plug and the outer edge of the distal end of the balloon member, the radial gap allowing rotational movement of the guiding member relative to the balloon member while providing resistance to flow of pressurized balloon fluid to minimize leakage of balloon fluid through the distal end of the balloon member.

11. The catheter of claim 1, and further including:
a flexible, helical coil member having a proximal end and a distal end, the coil member, being mounted on the distal end of the guiding member such that the proximal end of the coil member extends about the portion of the guiding member and the second sealing plug extends about a segment of the coil member.

12. The catheter of claim 1 wherein the first sealing plug includes a tapered portion that decreases distally and matches a taper at an inner edge of the distal end of the balloon member.

13. The catheter of claim 1 wherein each of the first and second sealing plugs is radiopaque to facilitate fluoroscopy viewing of the catheter.

14. The catheter of claim 1 wherein the tubular member is formed of a super elastic alloy.

15. A non-over-the-wire angioplasty catheter which is adapted to be inserted into a patient's vascular system, the catheter comprising:
an elongate flexible tubular member having an interior passage extending form a proximal end to a distal end;
a core wire having a smaller diameter than the tubular member and having a proximal end and a distal end, the core wire having its proximal end secured tot he tubular member adjacent to the distal end thereof, with the core wire extending distally beyond the distal end of the tubular member;
a flexible waist tube having a proximal end and a distal end, the waist tube having its proximal end sealably connected to the tubular member adjacent to the distal end thereof, the waist tube extending distally beyond the distal end of the tubular member about the core wire to define a distal interior passage in fluid communication with the interior passage of the tubular member, with the distal end of the waist tube terminating proximally of the distal end of the core wire;
an inflatable balloon member extending around a section of the core wire and having an interior in fluid communication with the distal interior passage of the waist tube, the balloon member including a proximal end sealably connected to the distal end of the waist tube and a distal end extending coaxially about a portion of the core wire so as to allow rotational movement of the core wire relative to the balloon member and thereby prevent twisting of the balloon member as the catheter is maneuvered through a vascular system of a patient; and
a first sealing plug secured to the guiding member immediately, proximally of the distal end of the balloon member, the first sealing plug defining a first stop that prevents the balloon member and waist tube from being displaced proximally along the core wire as the catheter is being maneuvered through a vascular system of a patient; and
a second sealing plug secured to the guiding member immediately, distally of the distal end of the balloon member, the second sealing plug defining a second stop that prevents the balloon member and waist tube form being displaced distally along the core wire as the catheter is being maneuvered through a vascular system of a patient.

16. The catheter of claim 15 wherein the tubular member is formed of a super elastic alloy.

* * * * *

UNITED STATES PATENT AND TRADEMARK OFFICE
CERTIFICATE OF CORRECTION

PATENT NO. : 5,312,340
DATED : May 17, 1994
INVENTOR(S) : Peter T. Keith

It is certified that error appears in the above-identified patent and that said Letters Patent is hereby corrected as shown below:

Column 8, line 60, delete "tot he" and insert --to the--.

Column 9, line 9, delete "claim wherein" and insert --claim 1 wherein--.

Column 9, line 53, delete "guiding relative" and insert --guiding member relative--.

Column 10, line 26, delete "tot he" and insert --to the--.

Column 10, line 62, delete "form" and insert --from--.

Signed and Sealed this

Sixth Day of September, 1994

Attest:

BRUCE LEHMAN

Attesting Officer

Commissioner of Patents and Trademarks